(12) United States Patent
Qu

(10) Patent No.: US 8,785,404 B2
(45) Date of Patent: Jul. 22, 2014

(54) UREA COMPOUNDS

(71) Applicant: Eli Lilly and Company, Indianapolis, IN (US)

(72) Inventor: Fucheng Qu, Carmel, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 14/035,997

(22) Filed: Sep. 25, 2013

(65) Prior Publication Data

US 2014/0100179 A1 Apr. 10, 2014

Related U.S. Application Data

(60) Provisional application No. 61/710,123, filed on Oct. 5, 2012.

(51) Int. Cl.
*C07D 487/10* (2006.01)
*C07H 17/02* (2006.01)
*A61K 31/70* (2006.01)

(52) U.S. Cl.
CPC ............... *C07H 17/02* (2013.01); *A61K 31/70* (2013.01)
USPC ........................................... 514/27; 536/17.4

(58) Field of Classification Search
CPC .................................. C07H 17/02; C07D 487/10
USPC ........................................... 514/27; 536/17.4
See application file for complete search history.

(56) References Cited

U.S. PATENT DOCUMENTS

| | | | |
|---|---|---|---|
| 7,087,579 B2 | 8/2006 | Nishimura et al. | |
| 7,115,575 B2 | 10/2006 | Fujikura et al. | |
| 7,217,697 B2 | 5/2007 | Shiohara et al. | |
| 7,375,087 B2 | 5/2008 | Teranishi et al. | |
| 7,635,684 B2 | 12/2009 | Fushimi et al. | |
| 7,655,632 B2 | 2/2010 | Teranishi et al. | |
| 7,820,804 B2 | 10/2010 | Brummerhop et al. | |
| 2010/0279962 A1 | 11/2010 | Takeuchi et al. | |
| 2013/0303471 A1 | 11/2013 | Qu et al. | |

FOREIGN PATENT DOCUMENTS

| | | |
|---|---|---|
| EP | 1544208 A1 | 6/2005 |
| EP | 1548024 A1 | 6/2005 |
| WO | 2004019958 A1 | 3/2004 |
| WO | 2007136116 A2 | 11/2007 |
| WO | 2010095768 A1 | 8/2010 |
| WO | 2011039338 A2 | 4/2011 |

OTHER PUBLICATIONS

Chao, Edward C. et al, SGLT2 Inhibition—a novel strategy for diabetes treatment, Nature Reviews, 2010, vol. 9, p. 552-559.

*Primary Examiner* — Ganapathy Krishnan
(74) *Attorney, Agent, or Firm* — Nelsen L. Lentz

(57) ABSTRACT

The present invention provides a compound of Formula I:

Formula I

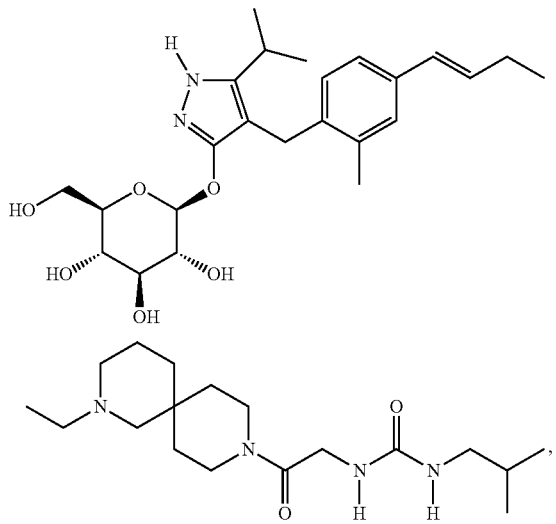

or a pharmaceutically acceptable salt thereof.

4 Claims, No Drawings

UREA COMPOUNDS

The present invention relates to novel urea compounds, to pharmaceutical compositions comprising the compounds, to methods of using the compounds to treat physiological disorders, and to intermediates and processes useful in the synthesis of the compounds.

The present invention is in the field of treatment of diabetes and other diseases and disorders associated with hyperglycemia. Diabetes is a group of diseases that is characterized by high levels of blood glucose. It affects approximately 25 million people in the United States and is also the $7^{th}$ leading cause of death in U.S. according to the 2011 National Diabetes Fact Sheet (U.S. Department of Health and Human Services, Centers for Disease Control and Prevention). Sodium-coupled glucose cotransporters (SGLT's) are one of the transporters known to be responsible for the absorption of carbohydrates, such as glucose. More specifically, SGLT1 is responsible for the transport of glucose across the brush border membrane of the small intestine Inhibition of SGLT1 may result in reduced absorption of glucose in the small intestine, thus providing a useful approach to treating diabetes.

U.S. Pat. No. 7,655,632 discloses certain pyrazole derivatives with human SGLT1 inhibitory activity which are further disclosed as useful for the prevention or treatment of a disease associated with hyperglycemia, such as diabetes. In addition, WO 2011/039338 discloses certain pyrazole derivatives with SGLT1/SGLT2 inhibitor activity which are further disclosed as being useful for treatment of bone diseases, such as osteoporosis.

There is a need for alternative drugs and treatment for diabetes. The present invention provides novel inhibitors of SGLT1 which may be suitable for the treatment of diabetes.

Accordingly, the present invention provides a compound of Formula I:

treating impaired glucose tolerance (IGT), impaired fasting glucose (IFG), or metabolic syndrome in a patient comprising administering to a patient in need of such treatment an effective amount of a compound of Formula I, or a pharmaceutically acceptable salt thereof.

Furthermore, this invention provides a compound of Formula I or a pharmaceutically acceptable salt thereof for use in therapy, in particular for the treatment of diabetes. In addition, this invention provides a compound of Formula I or a pharmaceutically acceptable salt thereof for use in the treatment of type 1 diabetes. In addition, this invention provides a compound of Formula I or a pharmaceutically acceptable salt thereof for use in the treatment of type 2 diabetes. This invention also provides the use of a compound of Formula I, or a pharmaceutically acceptable salt thereof, for the manufacture of a medicament for the treatment of diabetes. Furthermore, this invention provides the use of a compound of Formula I, or a pharmaceutically acceptable salt thereof, for the manufacture of a medicament for the treatment of type 1 diabetes. This invention also provides the use of a compound of Formula I, or a pharmaceutically acceptable salt thereof, for the manufacture of a medicament for the treatment of type 2 diabetes. The invention also provides the use of a compound of Formula I, or a pharmaceutically acceptable salt thereof, for the manufacture of a medicament for the treatment of IGT, IFG, or metabolic syndrome.

The invention further provides a pharmaceutical composition comprising a compound of Formula I, or a pharmaceutically acceptable salt thereof, in combination with one or more pharmaceutically acceptable carriers, diluents, or excipients. This invention also encompasses novel intermediates and processes for the synthesis of the compound of Formula I.

As used herein, the terms "treating" or "to treat" includes prohibiting, restraining, slowing, stopping, or reversing the progression or severity of an existing symptom or disorder.

Formula I

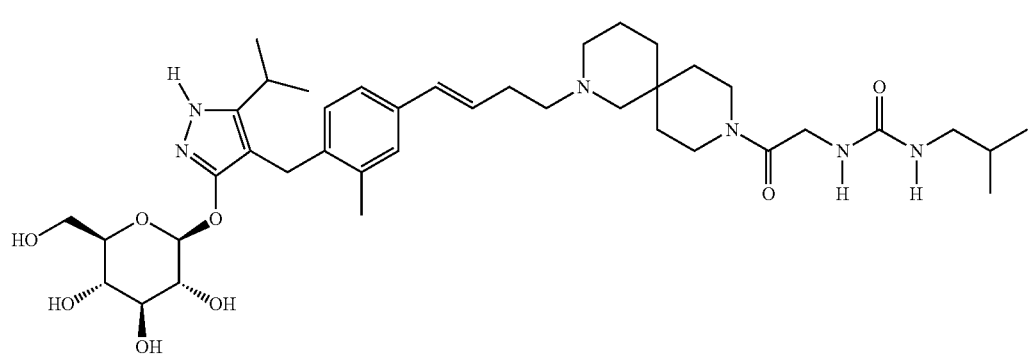

or a pharmaceutically acceptable salt thereof.

The present invention also provides a method of treating diabetes in a patient comprising administering to a patient in need of such treatment an effective amount of a compound of Formula I, or a pharmaceutically acceptable salt thereof. The present invention further provides a method of treating type 1 diabetes in a patient comprising administering to a patient in need of such treatment an effective amount of a compound of Formula I, or a pharmaceutically acceptable salt thereof. In addition, the present invention provides a method of treating type 2 diabetes in a patient comprising administering to a patient in need of such treatment an effective amount of a compound of Formula I, or a pharmaceutically acceptable salt thereof. The present invention also provides a method of As used herein, the term "patient" refers to a mammal, such as a mouse, guinea pig, rat, dog, or human. It is understood that the preferred patient is a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of Formula I are generally effective over a wide dosage range. For example, dosages per day normally fall within the range of about 0.01 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way.

The compounds of the invention are preferably formulated as pharmaceutical compositions administered by any route which makes the compound bioavailable. Most preferably, such compositions are for oral administration. Such pharmaceutical compositions and processes for preparing same are well known in the art. (See, e.g., Remington: The Science and Practice of Pharmacy (D. B. Troy, Editor, 21st Edition., Lippincott, Williams & Wilkins, 2006).

In a further aspect of the invention, the present compounds are administered in combination with one or more therapeutic agents, such as antidiabetic agents. Administration in combination includes simultaneous or sequential administration. In addition, simultaneous administration of the combination can be as a single combination dose or separate doses of each therapeutic agent. Examples of antidiabetic agents include metformin; a DPPIV inhibitor, such as sitagliptin or linagliptin; a sulfonylurea, such as glimepiride; a thiazolidinedione, such as pioglitazone; a basal insulin, such as glargine; a rapid acting insulin, such as HUMALOG or NOVOLOG; A GLP-1 agonist, such as exenatide or liraglutide; an SGLT2 inhibitor, such as dapagliflozin or empagliflozin; a glucagon receptor antagonist, such as LY2409021; and the like.

Compounds of Formula I are prepared as illustrated in the preparations, examples, and schemes below. The reagents and starting materials are readily available to one of ordinary skill in the art. All substituents, unless otherwise specified are as previously defined. It is understood that these schemes, preparations, and examples are not intended to be limiting to the scope of the invention in any way.

Examples of resolutions include selective crystallization techniques or chiral chromatography. (See, e.g. J. Jacques, et al., "Enantiomers, Racemates, and Resolutions", John Wiley and Sons, Inc., 1981, and E. L. Eliel and S. H. Wilen, "Stereochemistry of Organic Compounds", Wiley-Interscience, 1994). It should be further clear to one of ordinary skill in the art that separation and isolation, by chromatography, chiral chromatography or selective crystallization, of individual diastereomers or geometric isomers of Formula I or individual diastereomers or geometric isomers of intermediates leading to Formula I, can occur at any convenient point in the synthesis.

As used herein, "δ" refers to part per million down-field from tetramethylsilane; "min" refers to minute or minutes; "THF" refers to tetrahydrofuran; "MeOH" refers to methanol or methyl alcohol; "HPLC" refers to high-performance liquid chromatography; The term "Ac" refers to an acetyl substituent of the following structure:

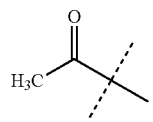

The term "BOC" refers to a t-butyloxycarbonyl protecting group.

Pharmaceutically acceptable salts and common methodology for preparing them are well known in the art. See, e.g., Gould, P. L., "Salt selection for basic drugs," International Journal of Pharmaceutics, 33: 201-217 (1986); Bastin et al. "Salt Selection and Optimization Procedures for Pharmaceutical New Chemical Entities," Organic Process Research and Development, 4: 427-435 (2000); and S. M. Berge, et al., "Pharmaceutical Salts," Journal of Pharmaceutical Sciences, Vol. 66, No. 1, January 1977. One skilled in the art of synthesis will appreciate that the compounds of Formula I as amines are organic bases, and that they are readily converted to and isolated as pharmaceutically acceptable salts, such as tartrate or HCl salts, using techniques and conditions well known to one of ordinary skill in the art.

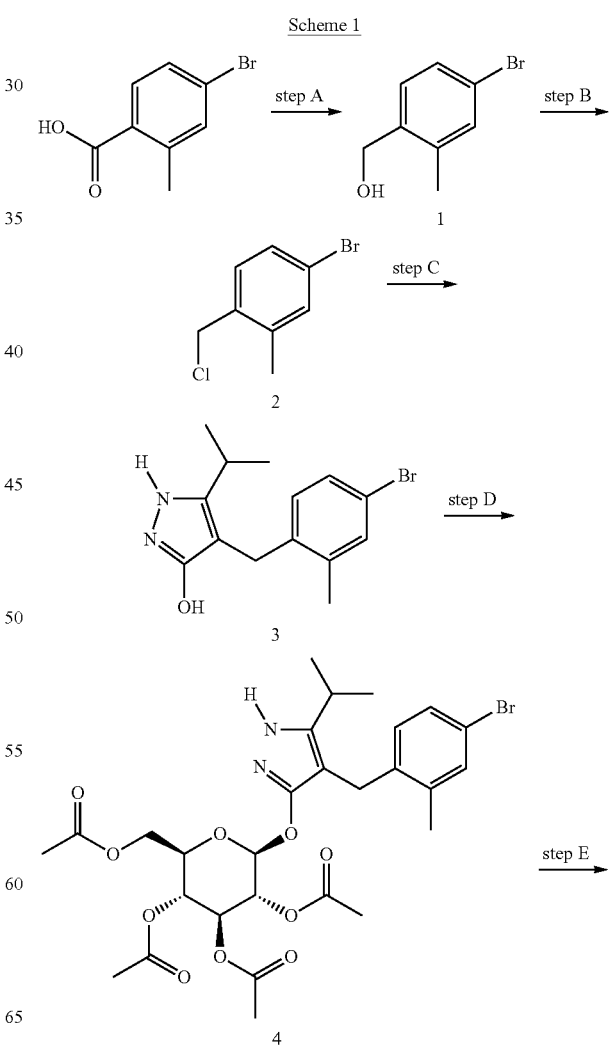

Scheme 1

-continued

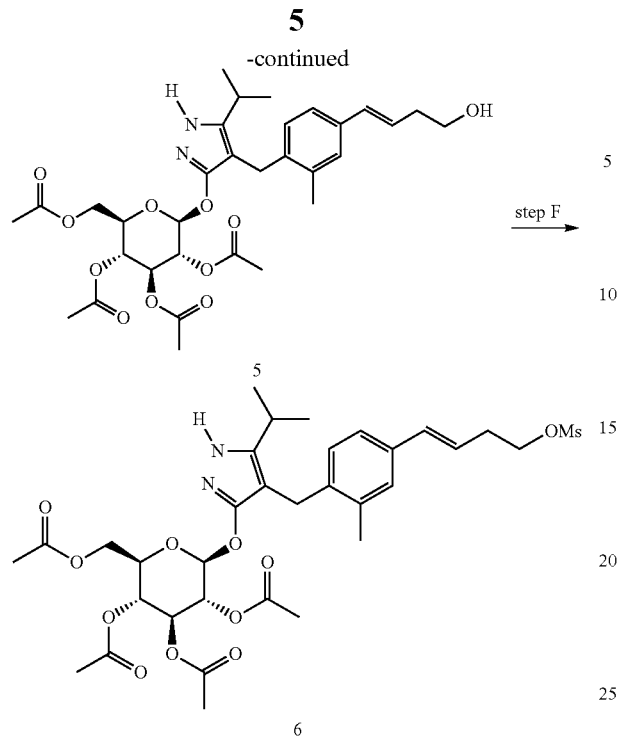

Preparation 1

(4-bromo-2-methyl-phenyl)methanol

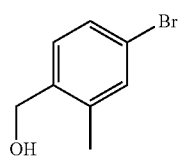

Scheme 1, step A: Add borane-tetrahydrofuran complex (0.2 mol, 200 mL, 1.0 M solution) to a solution of 4-bromo-2-methylbenzoic acid (39 g, 0.18 mol) in tetrahydrofuran (200 mL). After 18 hours at room temperature, remove the solvent under reduced pressure to provide a solid. Purify by flash chromatography to yield the title compound as a white solid (32.9 g, 0.16 mol). $^1$H NMR (CDCl$_3$): δ 1.55 (s, 1H), 2.28 (s, 3H), 4.61 (s, 2H), 7.18-7.29 (m, 3H).

Alternative Synthesis of (4-bromo-2-methyl-phenyl)methanol

Scheme 1, step A: Borane-dimethyl sulfide complex (2M in THF; 1150 mL, 2.3 mol) is added over 1.5 hours to a solution of 4-bromo-2-methylbenzoic acid (250 g, 1.16 mol) in anhydrous tetrahydrofuran (1500 mL) at 0° C. The reaction is allowed to warm slowly to ambient temperature and stirred overnight. The solution is cooled to −10° C. and water (500 mL) is added very slowly. Further water (5000 mL) is added and the mixture is extracted with ethyl acetate (2×5000 mL). The combined organic layers are washed with saturated aqueous NaCl solution (5000 mL) and dried over Na$_2$SO$_4$. Filtration and concentration under reduced pressure provides the title compound (226 g, 97% yield).

Preparation 2

4-bromo-1-chloromethyl-2-methyl-benzene

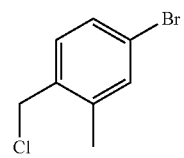

Scheme 1, step B: Add thionyl chloride (14.31 mL, 0.2 mol) to a solution of (4-bromo-2-methyl-phenyl)methanol (32.9 g, 0.16 mol) in dichloromethane (200 mL) and dimethylformamide (0.025 mol, 2.0 mL) at 0° C. After 1 hour at room temperature, pour the mixture into ice-water (100 g), extract with dichloromethane (300 mL), wash extract with 5% aq. sodium bicarbonate (30 mL) and brine (200 mL), dry over sodium sulfate, filter, and concentrate under reduced pressure to provide the crude title compound as a white solid (35.0 g, 0.16 mol). The material is used in the next step without further purification. $^1$H NMR (CDCl$_3$): δ 2.38 (s, 3H), 4.52 (s, 2H), 7.13-7.35 (m, 3H).

Alternative Synthesis of 4-bromo-1-(chloromethyl)-2-methyl-benzene

Scheme 1, step B: Methanesulfonyl chloride (171 mL, 2.11 mol) is added over 30 minutes to a mixture of (4-bromo-2-methyl-phenyl)methanol (250 g, 1.24 mol) and triethylamine (304 mL; 2.11 mol) in dichloromethane (2500 mL) cooled in ice/water. The mixture is allowed to warm to ambient temperature and is stirred for 16 hours. Water (5000 mL) is added and the product is extracted with dichloromethane (2×7000 mL). The combined organic layers are washed with saturated aqueous NaCl solution (5000 mL) and dried over Na$_2$SO$_4$. Filtration and concentration under reduced pressure provides a residue which is passed through a silica pad (eluting with hexane and ethyl acetate) to provide the title compound (234 g; 86% yield).

Preparation 3

4-[(4-bromo-2-methyl-phenyl)methyl]-5-isopropyl-1H-pyrazol-3-ol

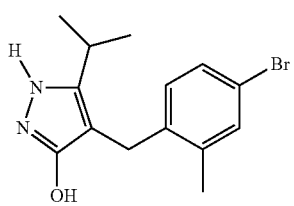

Scheme 1, step C: Add sodium hydride (8.29 g, 0.21 mol, 60% dispersion in oil) to a solution of methyl 4-methyl-3-oxovalerate (27.1 mL, 0.19 mol) in tetrahydrofuran at 0° C. After 30 min at room temperature, add a solution of 4-bromo-1-chloromethyl-2-methyl-benzene (35.0 g, 0.16 mol) in tetrahydrofuran (50 mL). Heat the resulting mixture at 70° C. overnight (18 hours). Add 1.0 M HCl (20 mL) to quench the reaction. Extract with ethyl acetate (200 mL), wash the extract with water (200 mL) and brine (200 mL), dry over $Na_2SO_4$, filter, and concentrate under reduced pressure. Dissolve the resulting residue in toluene (200 mL) and add hydrazine monohydrate (23.3 mL, 0.48 mol). Heat the mixture at 120° C. for 2 hours with a Dean-Stark apparatus to remove water. Cool and remove the solvent under the reduced pressure, dissolve the residue with dichloromethane (50 mL) and methanol (50 mL). Pour this solution slowly into a beaker with water (250 mL). Collect the resulting precipitated product by vacuum filtration. Dry in vacuo in an oven overnight at 40° C. to yield the title compound as a solid (48.0 g, 0.16 mol). MS (m/z): 311.0 (M+1), 309.0 (M−1).

Alternative Synthesis of 4-[(4-bromo-2-methyl-phenyl)methyl]-5-isopropyl-1H-pyrazol-3-ol Scheme 1, step C: A solution of 4-bromo-1-(chloromethyl)-2-methyl-benzene (500 g, 2.27 mol) in acetonitrile (2500 mL) is prepared. Potassium carbonate (941 g, 6.81 mol) and potassium iodide (450 g, 2.72 mol) are added and the mixture is stirred for 2 hours. Methyl 4-methyl-3-oxovalerate (340 mL; 2.39 mmol) is added. The resulting mixture is stirred at ambient temperature for 16 hours. Hydrochloric acid (2N; 8000 mL) is added to give pH 3. The solution is extracted with ethyl acetate (2×7000 mL), the organic phase is washed with brine (5000 mL), and dried over $Na_2SO_4$. The mixture is filtered and concentrated under reduced pressure. The residue is dissolved in toluene (2500 mL) and hydrazine monohydrate (340 mL, 6.81 mol) is added. The resulting mixture is heated at 110° C. and water is removed using a Dean-Stark apparatus. After 2 hours the mixture is cooled to 90° C. and additional hydrazine monohydrate (340 mL, 6.81 mol) is added, and the mixture is heated at 110° C. for 2 hours. The mixture is cooled and concentrated under reduced pressure. The residue is stirred with water (2500 mL) for 1 hour and the resulting solid is filtered, then triturated in hexane, and filtered to provide the title compound (460 g; 65% yield). Mass spectrum (m/z): 309/311 (M+1).

Preparation 4

4-(4-bromo-2-methylbenzyl)-5-(propan-2-yl)-1H-pyrazol-3-yl 2,3,4,6-tetra-O-acetyl-beta-D-glucopyranoside

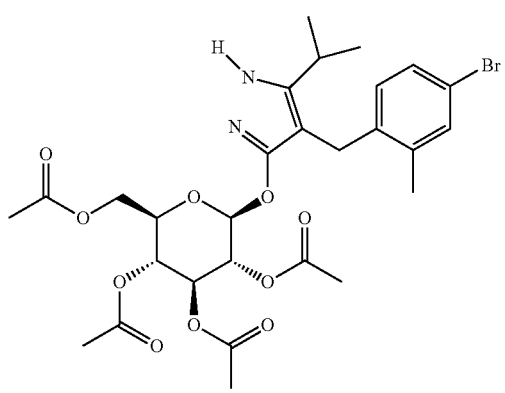 [SMILES: CC(=O)OC[C@H]1O[C@@H](OC(=N)/C(Cc2ccc(Br)cc2C)=C(\N)C(C)C)[C@H](OC(C)=O)[C@@H](OC(C)=O)[C@@H]1OC(C)=O]

Scheme 1, step D: To a 1 L flask, add 4-[(4-bromo-2-methyl-phenyl)methyl]-5-isopropyl-1H-pyrazol-3-ol (24 g, 77.6 mmol), 2,3,4,6-tetra-O-acetyl-alpha-D-glucopyranosyl bromide (50.4 g, 116 mmol), benzyltributylammonium chloride (5 g, 15.5 mmol), dichloromethane (250 mL), potassium carbonate (32 g, 323 mmol), and water (120 mL). Stir the reaction mixture overnight at room temperature. Extract with dichloromethane (450 mL). Wash the extract with water (300 mL) and brine (500 mL). Dry the organic phase over sodium sulfate, filter, and concentrate under reduced pressure. Purify the resulting residue by flash chromatography (silica gel, gradient ethyl acetate/dichloromethane from 10-70% over 20 min, 330 g column) to provide the title compound (36.5 g, 57 mmol). MS (m/z): 638.5 (M+1), 636.5 (M−1).

Alternative Synthesis of 4-(4-bromo-2-methylbenzyl)-5-(propan-2-yl)-1H-pyrazol-3-yl 2,3,4,6-tetra-O-acetyl-beta-D-glucopyranoside Scheme 1, step D: 4-[(4-Bromo-2-methyl-phenyl)methyl]-5-isopropyl-1H-pyrazol-3-ol (110 g, 356 mmol), 2,3,4,6-tetra-O-acetyl-alpha-D-glucopyranosyl bromide (204.8 g, 498 mmol), benzyltributylammonium chloride (17.2 g, 53.4 mmol), potassium carbonate (122.9 g, 889 mmol), dichloromethane (1100 mL), and water (330 mL) are combined and the mixture is stirred at 50° C. temperature for 16 hours. Further 2,3,4,6-tetra-O-acetyl-alpha-D-glucopyranosyl bromide (29.26 g, 71.2 mmol) is added and the mixture stirred at 55° C. for 3 hours. The mixture is cooled to ambient temperature and stirred overnight. Further 2,3,4,6-tetra-O-acetyl-alpha-D-glucopyranosyl bromide (29.26 g, 71.15 mmoles) is added and the mixture is heated to reflux for 1.5 hours. The mixture is cooled to ambient temperature and water (2000 mL) is added. The phases are separated and the aqueous is extracted with dichloromethane (500 mL). The combined organic layers are washed with water (2000 mL) and saturated aqueous NaCl solution (2000 mL). The solution is dried over $MgSO_4$ and filtered. The filtrate is concentrated under reduced to provide a solution of approximately 500 mL. This solution is poured onto a silica column and is purified by flash chromatography (5 Kg silica), eluting first with 100% dichloromethane, then with 40% ethyl acetate/dichloromethane, to provide the title compound (175 g, 77% yield). Mass spectrum (m/z): 639/641 (M+1).

Preparation 5

4-{4-[(1E)-4-hydroxybut-1-en-1-yl]-2-methylbenzyl}-5-(propan-2-yl)-1H-pyrazol-3-yl 2,3,4,6-tetra-O-acetyl-beta-D-glucopyranoside

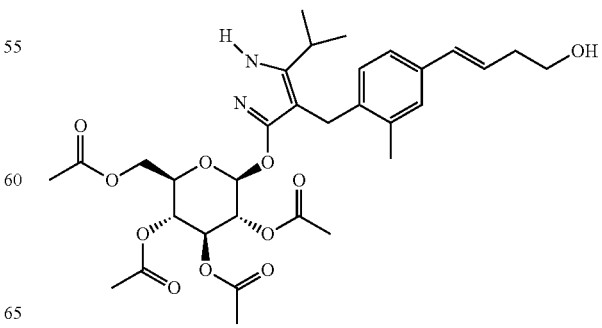

Scheme 1, step E: Add 3-buten-1-ol (6.1 mL, 70 mmol) to a solution of 4-(4-bromo-2-methylbenzyl)-5-(propan-2-yl)-1H-pyrazol-3-yl 2,3,4,6-tetra-O-acetyl-beta-D-glucopyranoside (15 g, 23.5 mmol) in acetonitrile (200 mL) and triethylamine (50 mL). Degas the solution with nitrogen over 10 minutes. Add tri-o-tolylphosphine (1.43 g, 4.7 mmol) and palladium acetate (526 mg, 2.35 mmol). After refluxing at 90° C. for 2 hours, cool and concentrate to remove the solvent under reduced pressure. Purify the resulting residue by flash chromatography (silica gel, gradient ethyl acetate/hexanes from 20-80% over 20 min, 330 g column) to provide the title compound (7.5 g, 11.9 mmol). MS (m/z): 631.2 (M+1), 629.2 (M−1).

Preparation 6

(3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl methanesulfonate

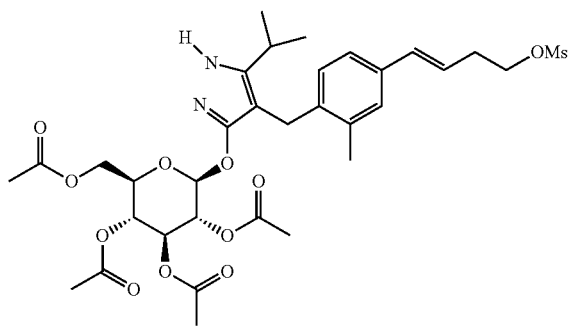 [SMILES: CC(=O)OC[C@H]1O[C@@H](OC(=N)/C(Cc2ccc(/C=C/CCOS(C)(=O)=O)cc2C)=C(\N)C(C)C)[C@H](OC(C)=O)[C@@H](OC(C)=O)[C@@H]1OC(C)=O]

Scheme 1, step F: Add methanesulfonyl chloride (1.35 g, 11.8 mmol) to a solution of 4-{4-[(1E)-4-hydroxybut-1-en-1-yl]-2-methylbenzyl}-5-(propan-2-yl)-1H-pyrazol-3-yl 2,3,4,6-tetra-O-acetyl-beta-D-glucopyranoside (1.5 g, 2.38 mmol) and triethylamine (5 g, 49.2 mmol) in dichloromethane (50 mL) at 0° C. After 30 minutes at room temperature, extract with dichloromethane (80 mL), and wash with water (80 mL) and brine (40 mL). Dry organic phase over sodium sulfate, filter and concentrate under reduced pressure. Purify the resulting residue by flash chromatography (silica gel, gradient ethyl acetate/dichloromethane from 10-65% over 20 min, 120 g column) to yield the title compound (5.4 g, 7.62 mmol). MS (m/z): 708.5 (M+1), 706.5 (M−1).

Scheme 2

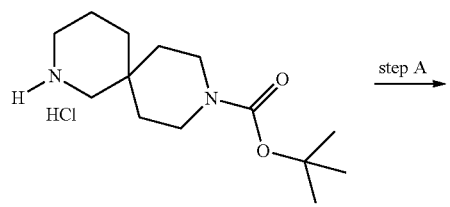

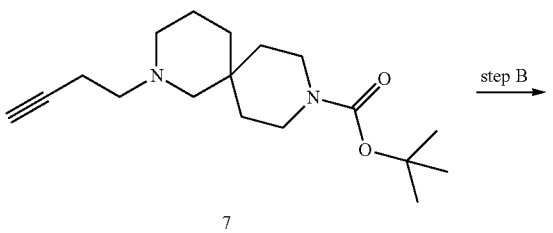

Preparation 7 tert-butyl 4-but-3-ynyl-4,9-diazaspiro[5.5]undecane-9-carboxylate

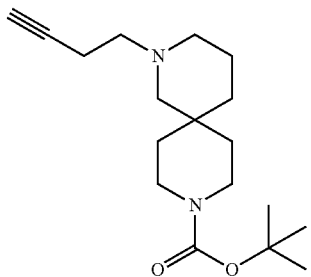 [SMILES: C#CCCN1CCCC2(CCN(C(=O)OC(C)(C)C)CC2)C1]

Scheme 2, step A: A mixture of tert-butyl 4,9-diazaspiro[5.5]undecane-9-carboxylate hydrochloride (170.00 g, 584.53 mmoles), cesium carbonate (476.13 g, 1.46 moles), and 4-bromobutyne (93.28 g, 701.43 mmoles) in acetonitrile (1.70 L) is heated to 60° C. and stirred at this temperature overnight. Further 4-bromobutyne (46.64 g, 350.72 mmoles) is added and the mixture is stirred at 60° C. overnight. The mixture is cooled and filtered. The filtrate is concentrated under reduced pressure and the residue dissolved in ethyl acetate (500 mL), washed with water (1 L), and saturated aqueous sodium chloride (1 L), then dried over MgSO$_4$, and filtered. The filtrate is concentrated under reduced pressure and the residue is purified by silica column chromatography eluting with 20 to 70% ethyl acetate in dichloromethane to provide the title compound (129 g, 72% yield). Mass spectrum (m/z): 307.25 (M+1).

Preparation 8 tert-butyl 4-[(E)-4-(4,4,5,5-tetramethyl-1,3,2-dioxaborolan-2-yl)but-3-enyl]-4,9-diazaspiro[5.5]undecane-9-carboxylate

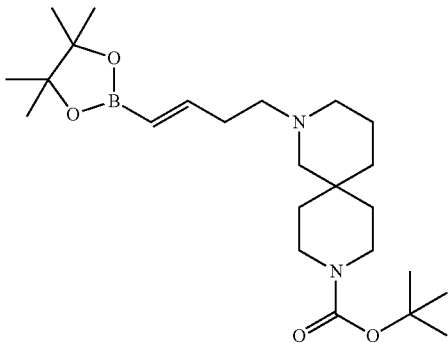 [SMILES: CC(C)(C)OC(=O)N1CCC2(CCCN(CC/C=C/B3OC(C)(C)C(C)(C)O3)C2)CC1]

Scheme 2, step B: Tert-butyl 8-but-3-ynyl-3,8-diazaspiro[5.5]undecane-3-carboxylate (129.00 g, 420.95 mmoles), triethylamine (5.87 mL, 42.10 mmoles), and zirconocene chloride (10.86 g, 42.10 mmoles) are combined. To this is added 4,4,5,5-tetramethyl-1,3,2-dioxaborolane (64.13 mL 442.00 mmoles) via syringe. The reaction is then heated to 65° C. and stirred at this temperature for 24 hours. The heat is turned off and the reaction allowed to stir at ambient temperature for a further 24 hours. Dichloromethane (500 mL) is added and the resulting solution is filtered through a 10 cm pad of silica eluting with 20% ethyl acetate in dichloromethane (3×500 mL). The filtrate is concentrated under reduced pressure to provide the title compound (163.5 g; Yield 89%). Mass spectrum (m/z): 435.35 (M+1).

Scheme 3

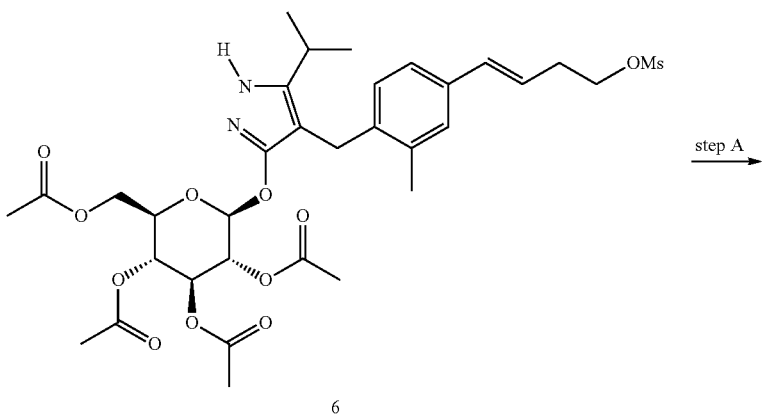

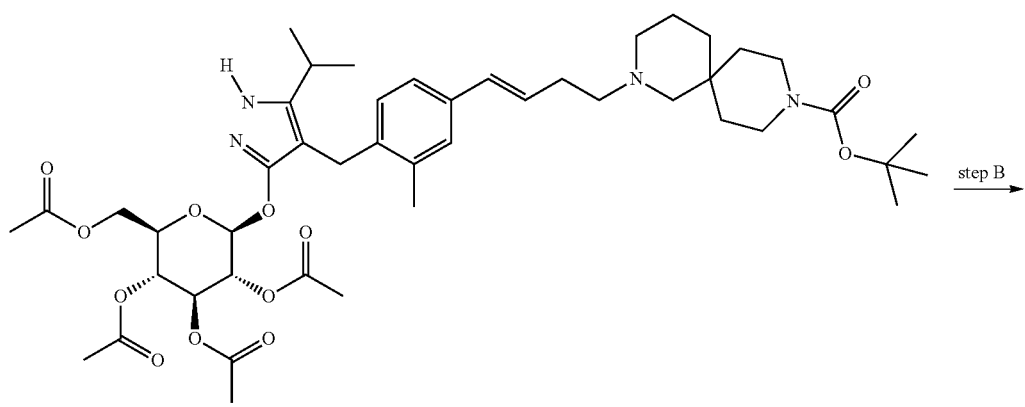

-continued
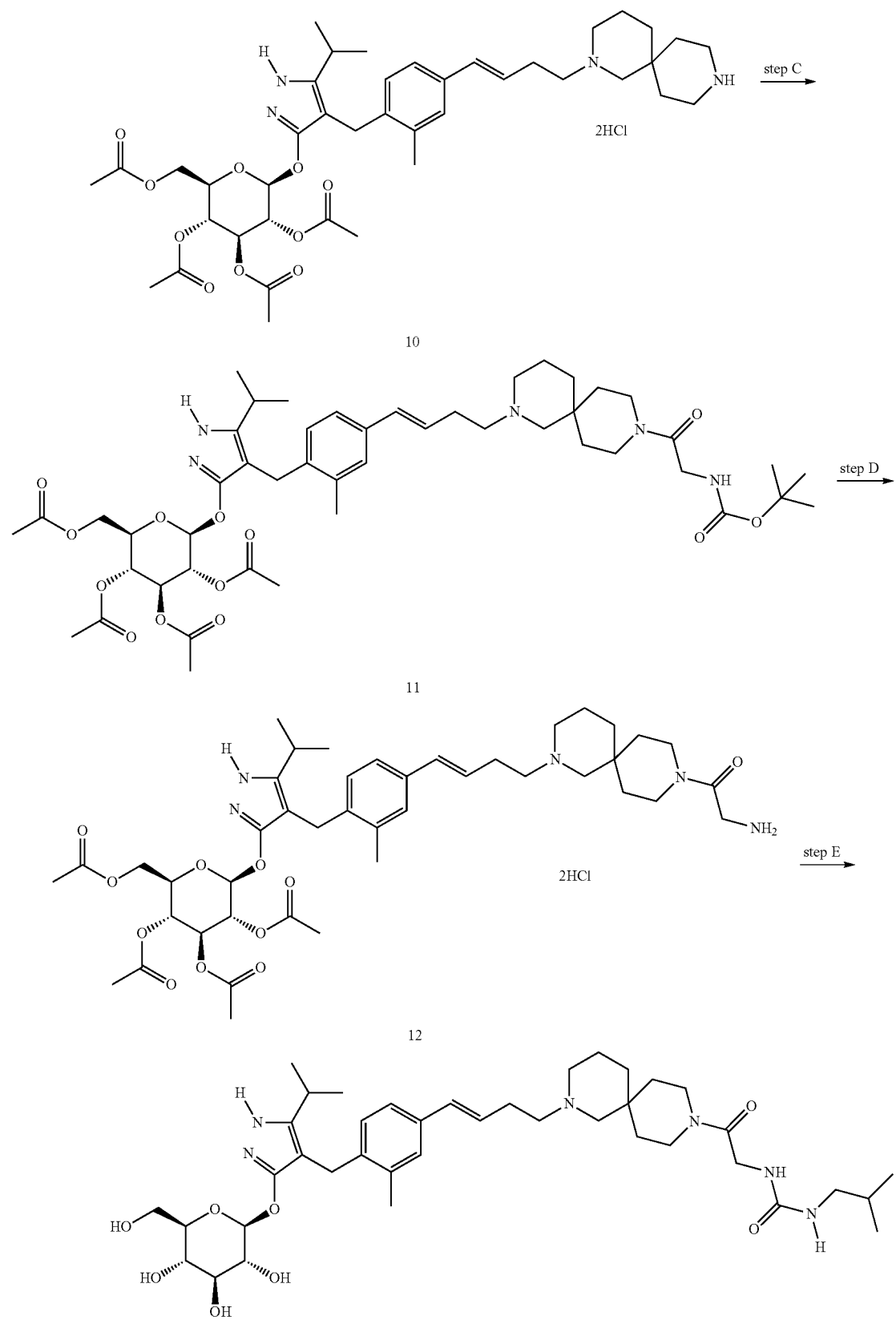

Preparation 9 tert-butyl 2-{(3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl}-2,9-diazaspiro[5.5]undecane-9-carboxylate

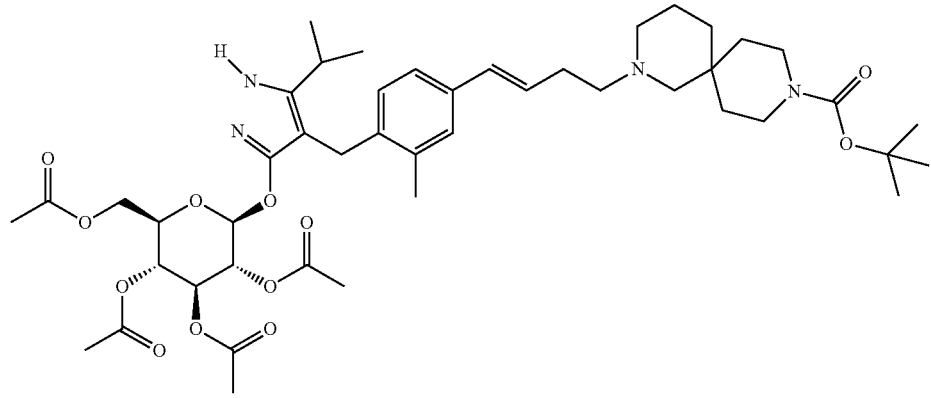 [SMILES: CC(=O)OC[C@H]1O[C@@H](OC(=N)/C(Cc2ccc(/C=C/CCN3CCCC4(CCN(C(=O)OC(C)(C)C)CC4)C3)cc2C)=C(\N)C(C)C)[C@H](OC(C)=O)[C@@H](OC(C)=O)[C@@H]1OC(C)=O]

Scheme 3, step A: Heat a mixture of (3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl methanesulfonate (1.0 g, 1.41 mmol), tert-butyl 2,9-diazaspiro[5.5]undecane-9-carboxylate hydrochloride (451 mg, 1.55 mmol), and diisopropylethylamine (730 mg, 5.64 mmol) in acetonitrile (4 mL) at 80° C. overnight. Remove the solvent under the reduced pressure. Purify the resulting residue by flash chromatography (silica gel, gradient ethyl acetate/dichloromethane from 25-85% over 15 min, then with methanol/dichloromethane from 1-3% over 10 min, 40 g column) to provide the title compound (630 mg, 0.73 mmol). MS (m/z): 867.2, 868.4 (M+1), 865.2, 866.4 (M−1).

Alternative Synthesis of tert-butyl 2-{(3E)-4-[3-methyl-4-({5-(propan-2-yl)-3-[2,3,4,6-tetra-O-acetyl-beta-D-glucopyranosyl)oxy]-1H-pyrazol-4-yl}methyl)phenyl]but-3-en-1-yl}-2,9-diazaspiro[5.5]undecane-9-carboxylate Scheme 3, step A: A flask is charged with 4-(4-bromo-2-methylbenzyl)-5-(propan-2-yl)-1H-pyrazol-3-yl 2,3,4,6-tetra-O-acetyl-beta-D-glucopyranoside (35.00 g, 54.73 mmoles), tert-butyl 8[(E)-4-(4,4,5,5-tetramethyl-1,3,2-dioxaborolan-2-yl)but-3-enyl]-3,8-diazaspiro[5.5]undecane-3-carboxylate (29.72 g, 68.41 mmoles), potassium carbonate (22.69 g, 164.19 mmoles), tetrahydrofuran (350.00 mL), and water (70.00 mL). The resulting solution is degassed. Pd(OAc)$_2$ (245.75 mg, 1.09 mmoles) and 2-dicyclohexylphosphino-2',4',6'-tri-1-propyl-1,1'-biphenyl (1.04 g, 2.19 mmoles) are then added and the solution is degassed again. The mixture is heated to reflux and stirred overnight. The mixture is cooled to room temperature and concentrated under reduced pressure. Water (400 mL) is added to the residue and the mixture extracted with ethyl acetate (2×500 mL then 200 mL). The combined organic extracts are washed with brine, dried over Na$_2$SO$_4$, filtered, and concentrated under reduced pressure to provide the title compound (50.0 g~about 80% purity). Mass spectrum (m/z): 867 (M+1). The compound can be purified by flash column chromatography (silica gel) eluting with ethyl acetate.

Preparation 10

4-{4-[(1E)-4-(2,9-diazaspiro[5.5]undec-2-yl)but-1-en-1-yl]-2-methylbenzyl}-5-(propan-2-yl)-1H-pyrazol-3-yl 2,3,4,6-tetra-O-acetyl-beta-D-glucopyranoside dihydrochloride

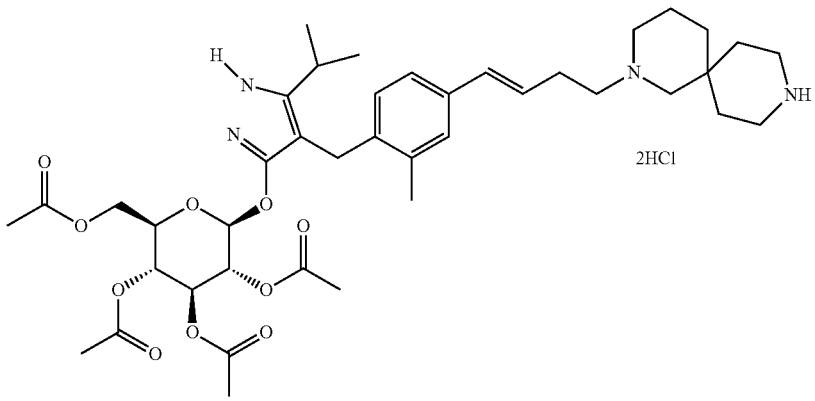 [SMILES: CC(=O)OC[C@H]1O[C@@H](OC(=N)/C(Cc2ccc(/C=C/CCN3CCCC4(CCNCC4)C3)cc2C)=C(\N)C(C)C)[C@H](OC(C)=O)[C@@H](OC(C)=O)[C@@H]1OC(C)=O]

Scheme 3, step B: Add hydrogen chloride (4.0 M solution in 1,4-dioxane, 1.5 mL, 5.8 mmol) to a solution of tert-butyl 2-{(3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl}-2,9-diazaspiro[5.5]undecane-9-carboxylate (500 mg, 0.58 mmol) in dichloromethane (20 mL). After 2 hours at room temperature, remove the solvent under reduced pressure to provide the title compound as solid (480 mg, 0.57 mmol). MS (m/z): 767.4 (M+1).

Preparation 11 tert-butyl[2-(2-{(3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl}-2,9-diazaspiro[5.5]undec-9-yl)-2-oxoethyl]carbamate Alternative Synthesis of tert-butyl[2-(2-{(3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl}-2,9-diazaspiro[5.5]undec-9-yl)-2-oxoethyl]carbamate Scheme 3, step C: Note that the starting material lot used for this transformation is about 64% pure (measured using HPLC UV absorbance). A flask is charged with tert-butyl 2-{(3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl}-2,9-diazaspiro[5.5]undecane-9-carboxylate (from preparation 9; 6.70 g, 7.73 mmoles) dichloromethane (40.00 mL) and hydrogen chloride (4M in dioxane; 9.66 mL, 38.64 mmoles). The mixture is stirred at ambient temperature for 3 hours. The solvent is removed under reduced pressure to provide 4-{4-[(1E)-4-(2,9-diazaspiro[5.5]undec-2-yl)but-1-en-1-yl]-2-methylbenzyl}-5-(propan-2-yl)-1H-pyrazol-3-yl 2,3,4,6-tetra-β-acetyl-beta-D-glucopyranoside dihydrochloride. To this is added dichloromethane (32.50 mL) and then triethylamine (5.39 mL, 38.70 mmoles). This mixture is stirred to give a

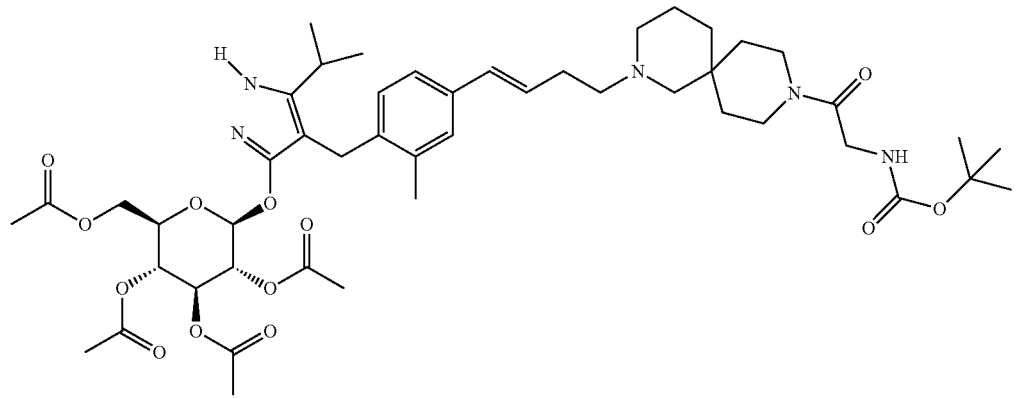 [SMILES: CC(=O)OC[C@H]1O[C@@H](OC(=N)/C(Cc2ccc(/C=C/CCN3CCCC4(CCN(C(=O)CNC(=O)OC(C)(C)C)CC4)C3)cc2C)=C(\N)C(C)C)[C@H](OC(C)=O)[C@@H](OC(C)=O)[C@@H]1OC(C)=O]

Scheme 3, step C: Add O-(7-azabenzotriazol-1-yl)-N,N,N',N' tetramethyluronium hexafluorophosphate (HATU, 543 mg, 1.43 mmol) to a solution of 4-{4-[(1E)-4-(2,9-diazaspiro[5.5]undec-2-yl)but-1-en-1-yl]-2-methylbenzyl}-5-(propan-2-yl)-1H-pyrazol-3-yl 2,3,4,6-tetra-O-acetyl-beta-D-glucopyranoside dihydrochloride (1.0 g, 1.19 mmol), N-alpha-T-Boc-glycine (317 mg, 1.79 mmol), and diisopropylethylamine (769 mg, 5.95 mmol) in dichloromethane (10 mL). Stir the mixture at room temperature for 2.0 hours. Remove the solvent under the reduced pressure. Purify the resulting residue by flash chromatography (silica gel, gradient ethyl acetate/dichloromethane from 30-85% over 20 min, 40 g column) to provide the title compound (1.0 g, 1.08 mmol). MS (m/z): 924.4 (M+1), 922.4 (M−1).

milky suspension. A second flask is charged with N-alpha-T-BOC-glycine (1.63 g, 9.29 mmoles), then dichloromethane (32.50 mL), and then 1,1'-carbonyldiimidazole (1.57 g, 9.67 mmoles). The mixture is stirred for 15 minutes. The glycine mixture is then added to the amine mixture, and the reaction is stirred rapidly for 15 minutes. Saturated aqueous NaHCO$_3$ (25 mL) is added and the mixture stirred for 5 minutes. The phases are separated and the aqueous phase is extracted with dichloromethane (25 mL). The organic phases are dried over Na$_2$SO$_4$, filtered, and concentrated. The residue is purified by flash column chromatography eluting with 40 to 100% ethyl acetate in iso-hexane, then further purified by reverse phase (C18) flash column chromatography eluting with 10 mM ammonium bicarbonate in water and acetonitrile to provide the title compound (3 g, 42% yield). Mass spectrum (m/z): 924.4 (M+1).

Preparation 12

4-(4-{(1E)-4-[9-(aminoacetyl)-2,9-diazaspiro[5.5]undec-2-yl]but-1-en-1-yl]-2-methylbenzyl}-5-(propan-2-yl)-1H-pyrazol-3-yl-2,3,4,6-tetra-O-acetyl-beta-D-glucopyranoside dihydrochloride

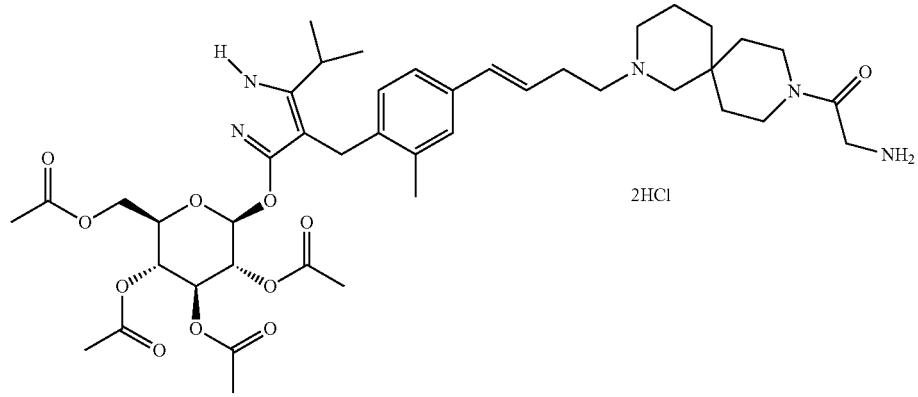 [SMILES: CC(=O)OC[C@H]1O[C@@H](OC(=N)/C(Cc2ccc(/C=C/CCN3CCCC4(CCN(C(=O)CN)CC4)C3)cc2C)=C(\N)C(C)C)[C@H](OC(C)=O)[C@@H](OC(C)=O)[C@@H]1OC(C)=O]

Scheme 3, step D: Add hydrogen chloride (4.0 M solution in 1,4-dioxane; 1.35 mL, 5.4 mmol) to a solution of tert-butyl [2-(2-{(3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl}-2,9-diazaspiro[5.5]undec-9-yl)-2-oxoethyl]carbamate (1.0 g, 1.08 mmol) in dichloromethane (10 mL). After 2 hours at room temperature, concentrate to remove the solvent under reduced pressure to provide the title compound as a solid (950 mg, 1.06 mmol). MS (m/z): 824.4 (M+1).

Alternative Synthesis of 4-(4-{(1E)-4-[9-(aminoacetyl)-2,9-diazaspiro[5.5]undec-2-yl]but-1-en-1-yl]-2-methylbenzyl}-5-(propan-2-yl)-1H-pyrazol-3-yl 2,3,4,6-tetra-O-acetyl-beta-D-glucopyranoside dihydrochloride Scheme 3, step D: A mixture of tert-butyl[2-(2-{(3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl}-2,9-diazaspiro[5.5]undec-9-yl)-2-oxoethyl] carbamate (12.10 g, 13.09 mmoles), dichloromethane (121.00 mL), and hydrogen chloride (4M in 1,4-dioxane; 16.37 mL, 65.47 mmoles) is stirred at ambient temperature for 4 hours. The mixture is concentrated under reduced pressure to provide the title compound (11.70 g; 99.6% yield). Mass spectrum (m/z): 824 (M+1 for free base).

EXAMPLE 1

1-(2-{2-[(3E)-4-(4-{[3-(beta-D-glucopyranosyloxy)-5-(propan-2-yl)-1H-pyrazol-4-yl]methyl}-3-methylphenyl)but-3-en-1-yl]-2,9-diazaspiro[5.5]undec-9-yl}-2-oxoethyl)-3-(2-methylpropyl)urea

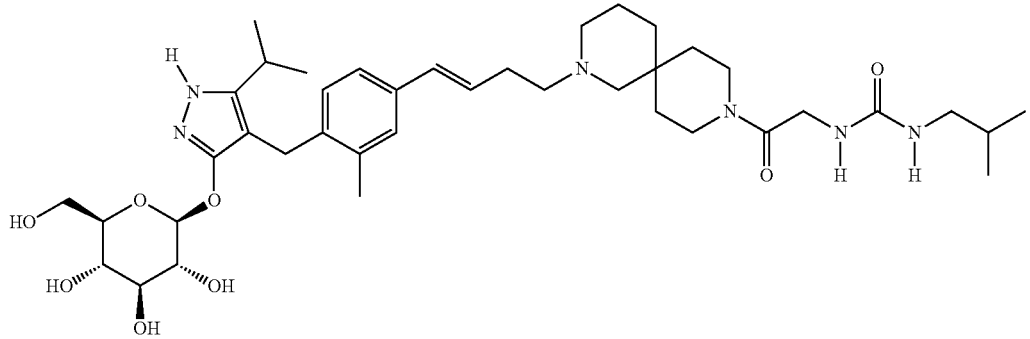 [SMILES: Cc1cc(/C=C/CCN2CCCC3(CCN(C(=O)CNC(=O)NCC(C)C)CC3)C2)ccc1Cc1c(O[C@@H]2O[C@H](CO)[C@@H](O)[C@H](O)[C@H]2O)n[nH]c1C(C)C]

Scheme 3, step E: Add isobutyl isocyanate (77 mg, 0.78 mmol) to a solution of 4-(4-{(1E)-4-[9-(aminoacetyl)-2,9-diazaspiro[5.5]undec-2-yl]but-1-en-1-yl]-2-methylbenzyl}-5-(propan-2-yl)-1H-pyrazol-3-yl 2,3,4,6-tetra-O-acetyl-beta-D-glucopyranoside dihydrochloride (350 mg, 0.39 mmol) and diisopropylethylamine (302 mg, 2.34 mmol) in dichloromethane (1.0 mL). After 30 min at room temperature, concentrate to dryness under the reduced pressure. Treat the residue with 2.0 M $NH_3$/methanol (1.0 mL) for 3 hours at room temperature, remove the solvent under the reduced pressure. Purify the resulting residue by preparative HPLC method: high pH, 29% B for 4 min, 29-44% B for 5 min @ 85 mL/min using a 30×75 mm, 5 um C18XBridge ODB column, solvent A—$H_2O$ w $NH_4HCO_3$ @ pH 10, solvent B—acetonitrile to yield the title compound as solid (134 mg, 0.18 mmol). MS (m/z): 755.2 (M+1), 753.2 (M−1).

$^1$H NMR (400.31 MHz, CD$_3$OD): 7.10 (d, J=1.3 Hz, 1H), 7.04 (dd, J=1.3, 8.0 Hz, 1H), 6.87 (d, J=8.0 Hz, 1H), 6.36 (d, J=15.6 Hz, 1H), 6.16 (dt, J=15.6, 6.5 Hz, 1H), 5.02 (m, 1H), 3.96 (d, J=16.4 Hz, 1H), 3.93 (d, J=16.4 Hz, 1H), 3.80 (d, J=12.4 Hz, 1H), 3.71 (d, J=17.0 Hz, 1H), 3.68 (d, J=17.0 Hz, 1H), 3.64 (m, 1H), 3.60-3.43 (m, 2H), 3.41-3.31 (m, 6H), 2.93 (d, J=6.8 Hz, 2H), 2.80 (m, 1H), 2.47-2.22 (m, 8H), 2.30 (s, 3H), 1.71 (m, 1H), 1.66-1.32 (m, 8H), 1.11 (d, J=7.0 Hz, 3H), 1.1 (d, J=7.0 Hz, 3H), 0.89 (d, J=6.7 Hz, 6H).

Alternative Synthesis of 1-(2-{2-[(3E)-4-(4-{[3-(beta-D-glucopyranosyloxy)-5-(propan-2-yl)-1H-pyrazol-4-yl]methyl}-3-methylphenyl]but-3-en-1-yl]-2,9-diazaspiro[5.5]undec-9-yl}-2-oxoethyl)-3-(2-methylpropyl)urea Scheme 3, step E: A mixture of 4-(4-{(1E)-4-[9-(aminoacetyl)-2,9-diazaspiro[5.5]undec-2-yl]but-1-en-1-yl]-2-methylbenzyl}-5-(propan-2-yl)-1H-pyrazol-3-yl 2,3,4,6-tetra-O-acetyl-beta-D-glucopyranoside dihydrochloride (11.70 g; 13.04 mmoles) in dichloromethane (33 mL) and diisopropylethylamine (13.65 mL; 78.27 mmoles) is stirred for 10 minutes to dissolve. The mixture is cooled to 5° C. and isobutyl isocyanate (2.59 g, 26.09 mmoles) is added dropwise over 5 minutes. When the addition is complete the cooling bath was removed. After 15 minutes, the mixture is concentrated under reduced pressure. The residue is treated with ammonia (2M in methanol; 35.00 mL, 70.00 mmoles) and stirred at ambient temperature for 1.5 hours. Further ammonia (2M in methanol; 35.00 mL, 70.00 mmoles) is added and the reaction is stirred overnight. The mixture is warmed to 40° C. and ammonia (2M in methanol; 35.00 mL, 70.00 mmoles) is added. The mixture is stirred for 160 minutes, and then concentrated. The residue is purified by reverse phase (C18) flash column chromatography eluting with 20:80 to 80:20 10 mM ammonium bicarbonate in water:acetonitrile to give the title compound (6.686 g, 68% yield). Mass spectrum (m/z): 755.5 (M+1).

Sodium-Dependent Glucose Transporter 1 (SGLT1) and SGLT2 Assays

The cDNA encoding human SGLT1 (slc5a1, NM_000343), human SGLT2 (slc5a2, NM_003041) and mouse SGLT1 (slc5a1, NM_019810.4) are purchased from Openbiosystems, Invitrogen and Openbiosystems, respectively. The cDNA is cloned into pcDNA3.1+ for mammalian expression and is stably transfected into Chinese hamster ovary (CHO)-K1 cells using standard mammalian transfection procedures. An SGLT-expressing sub-clone of each overexpressing cell line is selected based on resistance to neomycin (Geneticin, Invitrogen) and activity in the $^{14}$C-α-methyl-D-glucopyranoside ($^{14}$C-AMG) uptake assay (see below). Stable SGLT-expressing cells are maintained using standard cell culture techniques.

The SGLT activity is measured as sodium-dependent $^{14}$C-AMG uptake in the above cell lines described as follows. One hundred μL of culture medium containing 30,000 cells are seeded to each well of a 96-well BioCoat poly-D-lysine plate (Becton Dickson) and cultured at 37° C. overnight. The culture medium is aspirated and cells are washed twice with 200 μL of Reaction Buffer (140 mM NaCl, 2 mM KCl, 1 mM CaCl$_2$, MgCl$_2$, and 14 mM N-2-hydroethylpiperrazine-N'-2-ethanesulfonic acid (Hepes), pH 7.5). The excess buffer is tapped out onto paper towels. Thirty-five μL of Reaction Buffer are added to each well. Five μL of a 10% dimethylsufoxide (DMSO) in Reaction Buffer containing varying concentrations of test compound or no compound as a control, is dispensed into the each well. The reaction is initiated by adding 10 μL of $^{14}$C-AMG in Reaction Buffer to make a final concentration of 4 μM. The plate is incubated at 37° C. for 125 minutes. The reaction is terminated by aspirating off Reaction Buffer and then washed three times with 200 μL of ice cold Reaction Buffer. Manual aspiration is applied to ensure the complete removal of Reaction Buffer. Ten μL of 0.1 N NaOH is added to each well and then 100 μL of Supermix scintillation cocktail (PerkinElmer) is added. After mixing, the scintillation signal in the plate is counted in a MicroBeta (PerkinElmer). A ten-dose response curve is fitted to an empirical four-parameter model using ActivityBase (ID Business Solution) to determine the inhibitor concentration at half-maximal inhibition (IC$_{50}$).

TABLE 1

| In vitro potency of Example 1 against SGLT1 and SGLT2 | | | |
|---|---|---|---|
| Test Compound | Human SGLT1 IC$_{50}$, nM | Human SGLT2 IC$_{50}$, nM | Mouse SGLT1 IC$_{50}$, nM |
| Example 1 | 17.3 ± 16.2 (n = 5) | 171 ± 26 (n = 5) | 7.3 ± 2.9 (n = 5) |

The data in table 1 demonstrate that the compound of Example 1 inhibits human and mouse SGLT1 in vitro, and is more potent at human and mouse SGLT1 than at human SGLT2 in vitro.

Glucose Lowering Effects in Oral Glucose Tolerance Test (OGTT)

The test compound is formulated by adding a vehicle of 1% hydroxyethylcellulose, 0.25% Tween® 80 w/antifoam 0.05% to preweighed test compound to make a 1 mg/ml solution. The mixture is probe sonicated for approximately 1 minute. A stir bar is added, and the resulting suspension is stirred continuously throughout dosing.

Single housed C57Bl/6 mice are weighed and body weights used to determine study groups (n=5), within a working range of 26-30 g. After grouping, all mice are fasted overnight by removing access to food, late afternoon before test day. At the same time, two groups of mice are orally gavaged with 10 ml/kg test compound preparation or vehicle. Animals are dosed thirty seconds apart. These mice are used to demonstrate the compound's effects in an OGTT, 18 hours later. The following morning, the remaining mice are weighed and orally gavaged using the same protocol as the previous day.

At five, eight and eighteen hours after each respective compound treatment is started, a baseline blood sample is taken for measuring glucose (from the first animal, via tail snip). The animal is then immediately given an oral dose of 50% dextrose (Hospira®) at 3 g/kg. Blood samples are taken for glucose, exactly thirty seconds apart, by tail vein so that blood is collected in each animal at 20, 40, 60 and 120 minutes after the dextrose dose.

TABLE 2

Glucose lowering effects in OGTT.
Oral Glucose Tolerance Test Results Mean ± SE

| | Vehicle @ 5 hrs post Dose | Example 1 10 mg/kg @ 5 hr post Dose | Vehicle @ 8 hrs post Dose | Example 1 10 mg/kg @ 8 hrs post Dose | Vehicle @ 18 hrs post Dose | Example 1 10 mg/kg @ 18 hrs post Dose |
|---|---|---|---|---|---|---|
| Glucose (mg/dl) | | | | | | |
| 0 Minute | 74.5 ± 1.54 | 75.9 ± 3.21 | 75.0 ± 6.48 | 75.5 ± 4.42 | 69.7 ± 3.42 | 78.7 ± 8.81 |
| 20 Minute | 232.3 ± 13.51 | 124.7 ± 7.66* | 296.9 ± 26.4 | 142.4 ± 7.4** | 282.3 ± 12.8 | 196.0 ± 16.6** |
| 40 Minute | 189.5 ± 12.4 | 139.2 ± 7.69** | 240.0 ± 15.1 | 168.1 ± 8.37** | 241.6 ± 17.9 | 216.1 ± 15.0 |
| 60 Minute | 176.5 ± 14.8 | 133.2 ± 6.24** | 183.1 ± 12.9 | 171.2 ± 10.1 | 163.3 ± 9.77 | 188.7 ± 13.8 |
| 120 Minute | 104.1 ± 8.57 | 108.7 ± 4.93 | 109.7 ± 3.89 | 113.6 ± 4.25 | 102.5 ± 3.57 | 110.3 ± 5.74 |
| Baseline Adjusted AUC | 6475 ± 168 | 2815 ± 194** | 8819 ± 668 | 4147 ± 456** | 8626 ± 565 | 6194 ± 406* |
| Glucose (mg/dl) | | | | | | |
| Glucose Cmax | 232.3 ± 13.5 | 140.2 ± 7.48** | 296.9 ± 26.4 | 175.1 ± 9.3** | 283.2 ± 13.1 | 216.1 ± 15.0* |
| Time (minutes) | | | | | | |
| Glucose Tmax | 20 ± 0.0 | 56 ± 16 | 20 ± 0.0 | 52 ± 4.9** | 24 ± 4.0 | 44 ± 4.0* |

1 way ANOVA/Dunnett's *p < 0.05, **p < 0.01 compared to vehicle

As shown in table 1, the compound of example 1 delivers a decrease in the glucose excursion when an oral bolus of 50% dextrose (Hospira®) is given to a normal glycemic C57Bl/6 mouse five, eight or eighteen hours after administration. Example 1 also demonstrates a dose dependent decrease in baseline adjusted glucose area under the curve (AUC) during all three OGTTs. In addition, example 1 decreases the average maximum concentration of plasma glucose (Cmax) during all three OGTTs while increasing the average time that it takes for glucose to reach maximum concentration (Tmax).

I claim:

1. A compound of the formula:

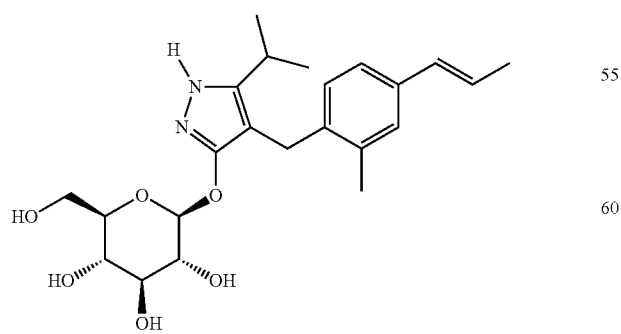

-continued

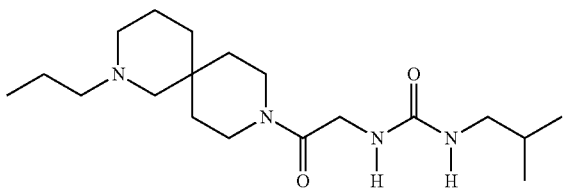

or a pharmaceutically acceptable salt thereof.

2. The compound according to claim 1 which is:

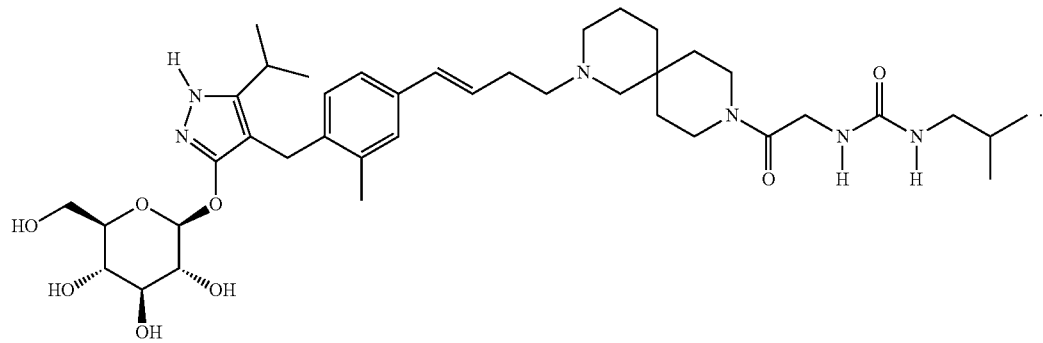 [SMILES: Cc1cc(/C=C/CCN2CCCC3(CCN(C(=O)CNC(=O)NCC(C)C)CC3)C2)ccc1Cc1c(O[C@@H]2O[C@H](CO)[C@@H](O)[C@H](O)[C@H]2O)n[nH]c1C(C)C]

3. A method of treating diabetes in a patient comprising administering to a patient in need of such treatment an effective amount of the compound, or pharmaceutically acceptable salt thereof, according to claim 1.

4. A pharmaceutical composition comprising the compound or a pharmaceutically acceptable salt thereof according to claim 1 in combination with one or more pharmaceutically acceptable carriers, diluents, or excipients.

* * * * *